United States Patent
Bjork et al.

(10) Patent No.: US 7,309,312 B2
(45) Date of Patent: Dec. 18, 2007

(54) APPARATUS FOR RETAINING OTHERWISE HAND-HELD RETRACTORS AND METHOD OF USE

(75) Inventors: Todd M. Bjork, River Falls, WI (US); Todd William Sharratt, Stillwater, MN (US); Christopher L. Berg, Crystal, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 61 days.

(21) Appl. No.: 11/034,234

(22) Filed: Jan. 12, 2005

(65) Prior Publication Data
US 2005/0272982 A1 Dec. 8, 2005

Related U.S. Application Data

(63) Continuation-in-part of application No. 10/936,865, filed on Sep. 9, 2004, now Pat. No. 6,932,765, which is a continuation of application No. 10/057,840, filed on Oct. 26, 2001, now abandoned.

(60) Provisional application No. 60/535,909, filed on Jan. 12, 2004.

(51) Int. Cl.
*A61B 1/32* (2006.01)

(52) U.S. Cl. .................. 600/231; 600/233

(58) Field of Classification Search ............ 600/231, 600/232, 233, 227, 217, 206
See application file for complete search history.

(56) References Cited

U.S. PATENT DOCUMENTS

| | | | |
|---|---|---|---|
| 2,313,164 A | 3/1943 | Nelson | 128/20 |
| 3,782,370 A | 1/1974 | McDonald | 128/20 |
| 3,844,550 A | 10/1974 | McGuire | 269/328 |
| 4,350,151 A | 9/1982 | Scott | 600/225 |
| RE32,021 E | 11/1985 | Scott, Jr. | 600/217 |
| 4,827,926 A | 5/1989 | Carol | 128/303 |
| 4,950,222 A | 8/1990 | Scott et al. | 600/21 |
| 5,020,195 A | 6/1991 | LeVahn | 24/514 |
| 5,104,103 A | 4/1992 | Auchinleck et al. | 269/74 |
| 5,307,790 A | 5/1994 | Byrne | 128/20 |
| 5,728,041 A | 3/1998 | Fowler, Jr. | 600/21 |
| 5,728,047 A | 3/1998 | Edoga | 600/227 |
| 5,755,661 A | 5/1998 | Schwartzman | 600/21 |
| 5,769,783 A | 6/1998 | Fowler | 600/226 |
| 5,785,649 A | 7/1998 | Fowler, Jr. | 600/233 |
| 5,857,965 A | 1/1999 | Rootman et al. | 600/233 |
| 5,899,425 A | 5/1999 | Corey Jr. et al. | 248/276.1 |
| 5,899,853 A | 5/1999 | Fowler, Jr. | 600/217 |
| 5,954,638 A | 9/1999 | Spranza, III | 600/201 |
| 5,954,639 A | 9/1999 | Gray | 600/233 |
| 5,964,697 A | 10/1999 | Fowler, Jr. | 600/210 |
| 5,964,698 A | 10/1999 | Fowler | 600/217 |
| 6,017,306 A | 1/2000 | Bigliani et al. | 600/234 |
| 6,077,221 A | 6/2000 | Fowler, Jr. | 600/233 |
| 6,090,043 A | 7/2000 | Austin et al. | 600/217 |
| 6,102,922 A | 8/2000 | Jakobsson et al. | 606/157 |
| 6,117,072 A | 9/2000 | Fowler, Jr. | 600/217 |
| 6,190,312 B1 | 2/2001 | Fowler, Jr. | 60/231 |
| 6,277,069 B1 | 8/2001 | Gray | 600/234 |
| 6,468,207 B1 | 10/2002 | Fowler, Jr. | 600/233 |
| 6,709,389 B2 | 3/2004 | Farasconi | 600/229 |
| 2002/0177754 A1 | 11/2002 | Phillips | 600/234 |

*Primary Examiner*—Cris Rodriguez
*Assistant Examiner*—Candice C Stokes
(74) *Attorney, Agent, or Firm*—Westman, Champlin & Kelly, P.A.

(57) ABSTRACT

A retractor retaining device retains an otherwise hand-held retractor in a retracting position within a surgical wound. The retractor retaining device includes a clamp that is attachable to a retractor support that is positioned about the wound. A retaining plate is attached to the clamp and engages a flexible loop. The flexible loop is detachably attached to the retaining plate for engaging a handle of the hand held retractor such that the hand held retractor is retained in the retracting position.

20 Claims, 8 Drawing Sheets

APPARATUS FOR RETAINING OTHERWISE HAND-HELD RETRACTORS AND METHOD OF USE

CROSS REFERENCE TO RELATED APPLICATION(S)

This application claims priority of U.S. Provisional Application No. 60/535,909 filed on Jan. 12, 2004 the content of which is hereby incorporated by reference in its entirety.

This application is also a continuation-in-part of application Ser. No. 10/936,865 filed on Sep. 9, 2004 now U.S. Pat. No. 6,932,765, which is hereby incorporated by reference in its entirety, which is a continuation of application Ser. No. 10/057,840 filed on Oct. 26, 2001 now abandoned, which is hereby incorporated by reference in its entirety.

BACKGROUND OF THE INVENTION

The present invention relates to surgical retractors, and to devices for holding surgical retractors in a retracting position.

Most improvements in surgical retractor supports or clamps to hold surgical retractors in a retraction position are directed to improvements on devices that have been used to mount retractors on retractor supports using rigid mechanical clamps for restraints. However, in certain situations, retractors are still manually held by a nurse or a surgeon since no clamp provides such versatile holding characteristics.

There are no devices that will retain a retractor in the retraction position that is otherwise manually held from a typical retractor support. The Edoga U.S. Pat. No. 5,728,047 describes the use of a belt on which various types of retractor retaining mechanism are shown, especially in FIGS. 7a through 7i. However, these retaining mechanisms do not address the problem of quickly and easily retaining an otherwise manually held retractor. Furthermore, the retractor handle has to be specially adapted to engage the fastening mechanism.

BRIEF SUMMARY OF THE INVENTION

The present invention includes a retractor retaining device for retaining an otherwise hand-held retractor in a retracting position within a surgical wound. The retractor retaining device includes a clamp that attaches to a retractor support that is positioned about the surgical wound. A retaining plate is attached to the clamp and engages a flexible loop. The flexible loop is detachably attached to the retaining plate for engaging a handle of the hand held retractor such that the hand held retractor is retained in the retracting position.

The present invention also includes a retraction device that includes a retractor support member positioned proximate a surgical wound. A clamp attaches to the retractor support member where the clamp has a retaining plate attached thereto. A retractor having a proximal end and a distal end for insertion into the surgical wound is secured in a retraction position with a flexible loop secured to the retaining plate and engaging the proximal end of the retractor.

The invention also includes a method of retaining a surgical retractor in the retraction position within the surgical wound. The method includes providing a support member near the surgical wound and then inserting a retractor within the surgical wound and manually positioning the retractor in a retraction position. The retractor is retained in the retraction position by securing a proximal end of the retractor in engagement with a flexible loop that is secured to a retaining plate attached to a clamp positioned on the support member.

DETAILED DESCRIPTION

Figure 1:
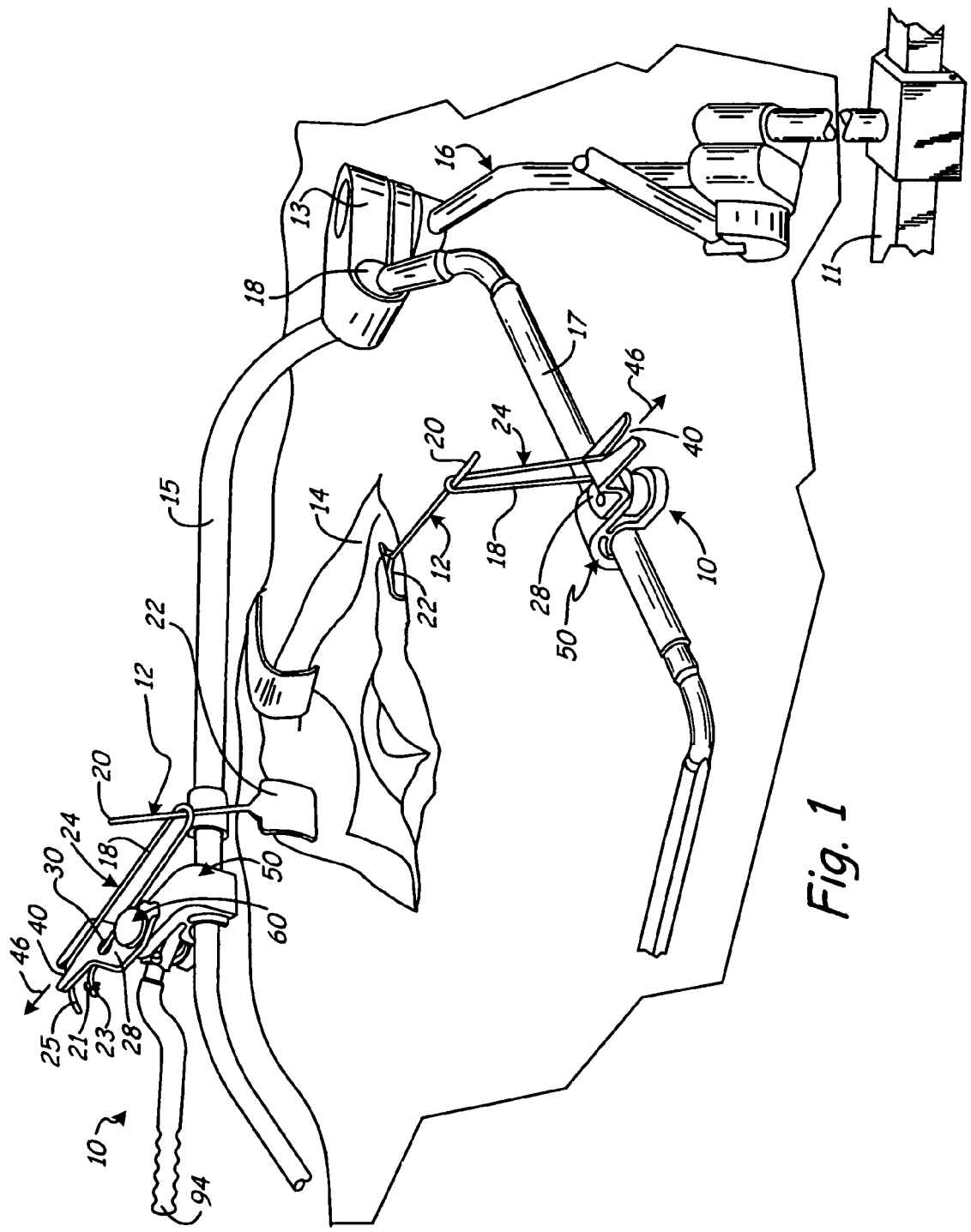
FIG. 1 is a perspective view of a retractor retaining device present invention in use.

The retractor retaining device of the present invention is generally illustrated in FIG. 1 at 10. The device 10 retains a retractor 12 in a retraction position within a surgical wound 14. The device 10 is used for retaining retractors that are otherwise manually held in the retraction position.

The retractor 12 is initially positioned within a surgical wound 14 and placed in the retraction position with manual force. The device 10 is then used to retain the retractor 12 which otherwise would have to be held in the retraction position manually by a doctor or a nurse.

The device 10 is mounted to a retractor support 16 that is positioned over or proximate to the surgical wound 14. The type of retractor support 16 is not particularly important to the present invention except that it provides a solid base to which the retaining device 10 is attached. However, the support 16 is preferably mounted to a surgical table 11 and includes substantially symmetric support arms 15, 17 having pivot balls (not shown) 18, respectively, for independently adjusting positions of the support arms 15, 17 where the pivot balls (not shown) 18 are secured in selected positions with a clamp 13. Examples of table mounted retractor supports which are suitable retractor supports are disclosed in U.S. Pat. Nos. 5,899,627 and 6,264,396 both of which are incorporated by reference in their entireties.

The essence of the present invention is to provide a structure and a method for retaining the retractor 12 that is normally held in a retraction position manually. The device 10 quickly engages the retractor 12 or quickly disengages from the retractor 12. The retractor 12 does not require a handle designed to be gripped by a specific retaining device and can therefore be of any shape. This purpose is accomplished by providing a loop 18 that extends from the support 16 and encircles a proximal end (handle) 20 of the retractor 12. The retractor 12 at a distal end (blade) 22 is inserted into the wound 14 and manual force is used to retract flesh and tissue. The loop 18 encircles the proximal end 20 of the retractor 12 and secures the retractor 12 in a retraction position.

Referring to FIGS. 1-5, the loop 18 is a portion of a cord 24. The cord 24 is secured to a retaining plate 28 attached to a clamp 50 that secures the retaining device 10 to the support 16. The cord 24 is removably attached to the retaining plate 28 by positioning a proximal end 25 of the cord 24 through an aperture 30 in a substantially vertical middle portion 32 of the retaining plate 28. A band 21 attached proximate a distal end 23 of the cord 24 engages a back surface 27 of the retaining plate 28 and prevents the distal end 23 of the cord 24 from passing through the aperture 30. The distal end 23 of the cord 24 is prevented from passing through the aperture 30 because a length of the band 21 is greater than a diameter of the aperture 30.

The band 21 allows the cord 24 to be easily replaced by pulling the proximal end 25 of the cord 24 through the aperture 30. The ability to replace the cord 24 is important for sterilization purposes to prevent contamination and infection as well as to replace worn cords.

Figure 4:
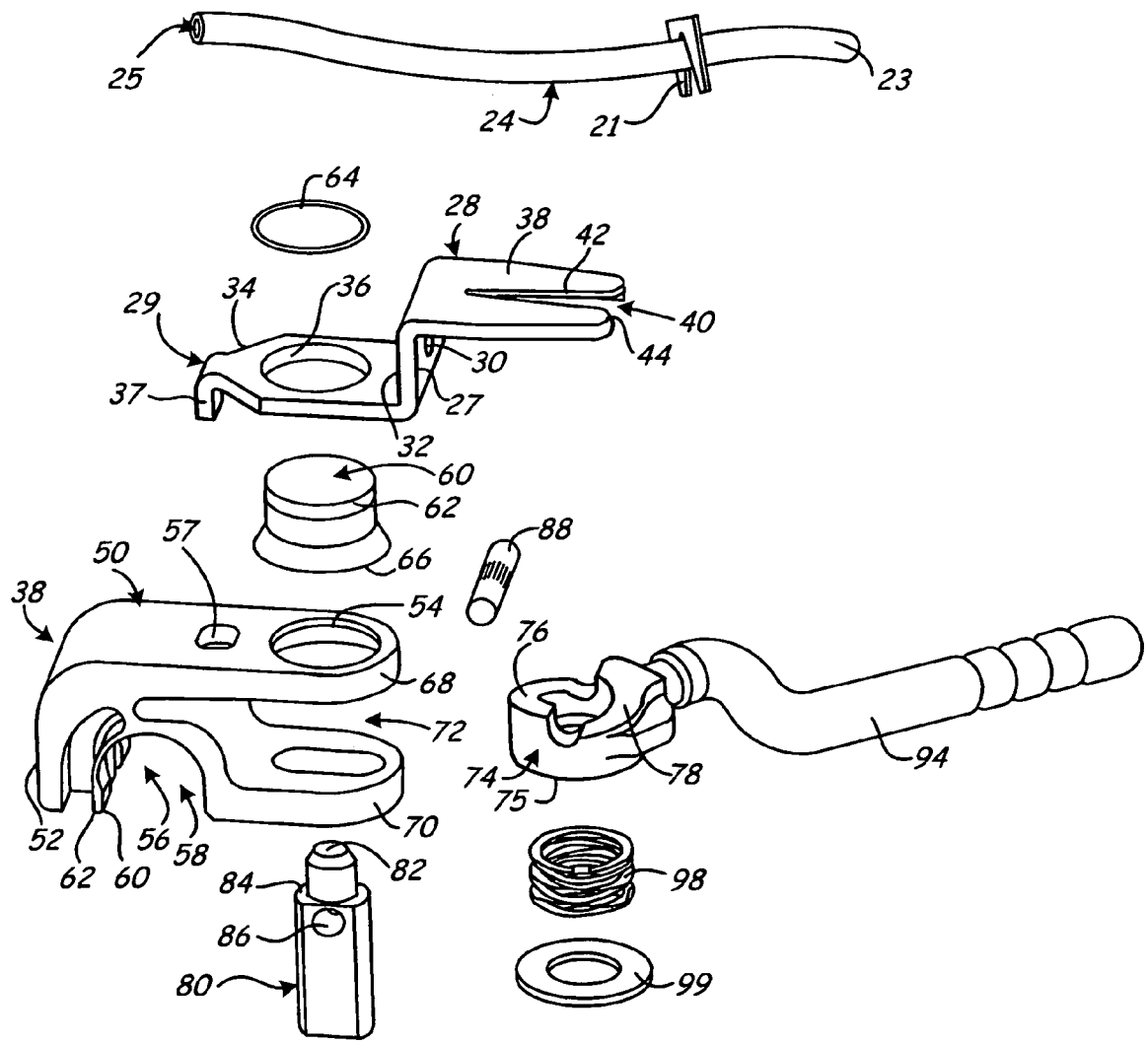
FIG. 4 is an exploded view of the retractor retaining device of the present invention.
Figure 5:
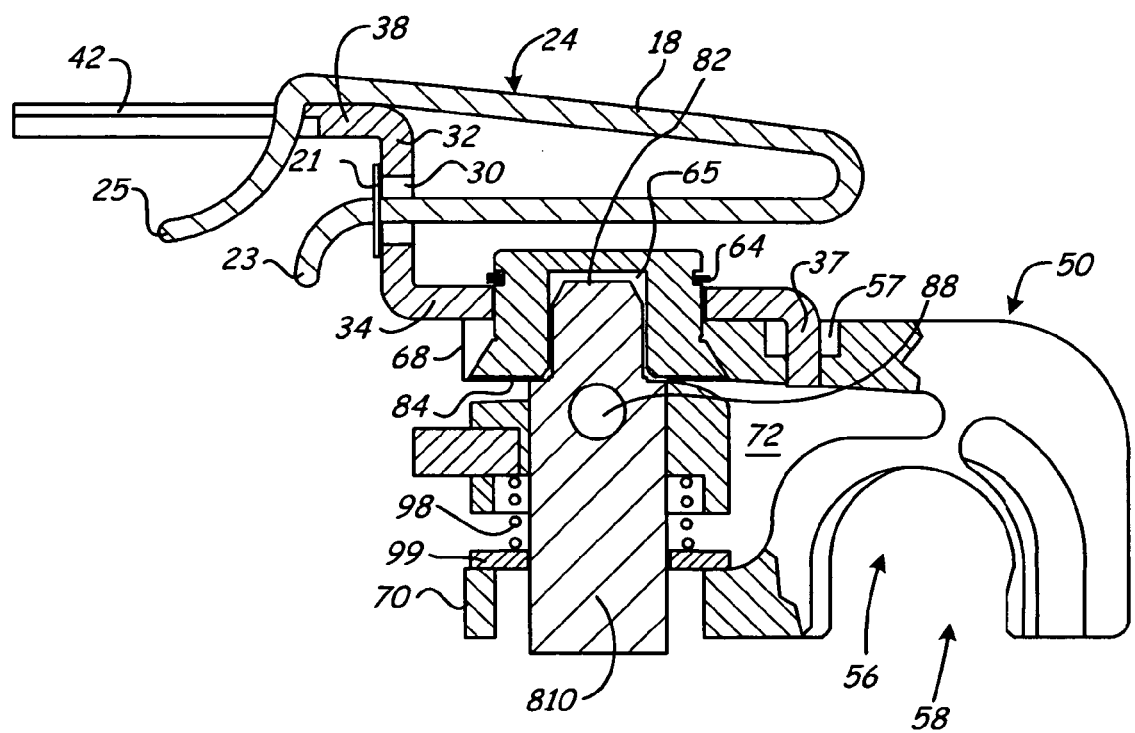
FIG. 5 is a sectional view of the retractor retaining device of the present invention.

Referring to FIGS. 4 and 5, the retaining plate 28 includes a through bore 36 in a lower portion 34 that accepts a peg 60 extending through a through bore 54 in an upper leg 68 of the clamp 50. The retaining plate 28 is secured to the clamp 50 with a snap ring 64 positioned within an annular groove 62 in the peg 60. The retaining plate 28 is secured in a selected rotational position by positioning a tab 37 at a proximal end 29 of the retaining plate 28 into a cavity 56 in the upper leg 68.

Figure 2:
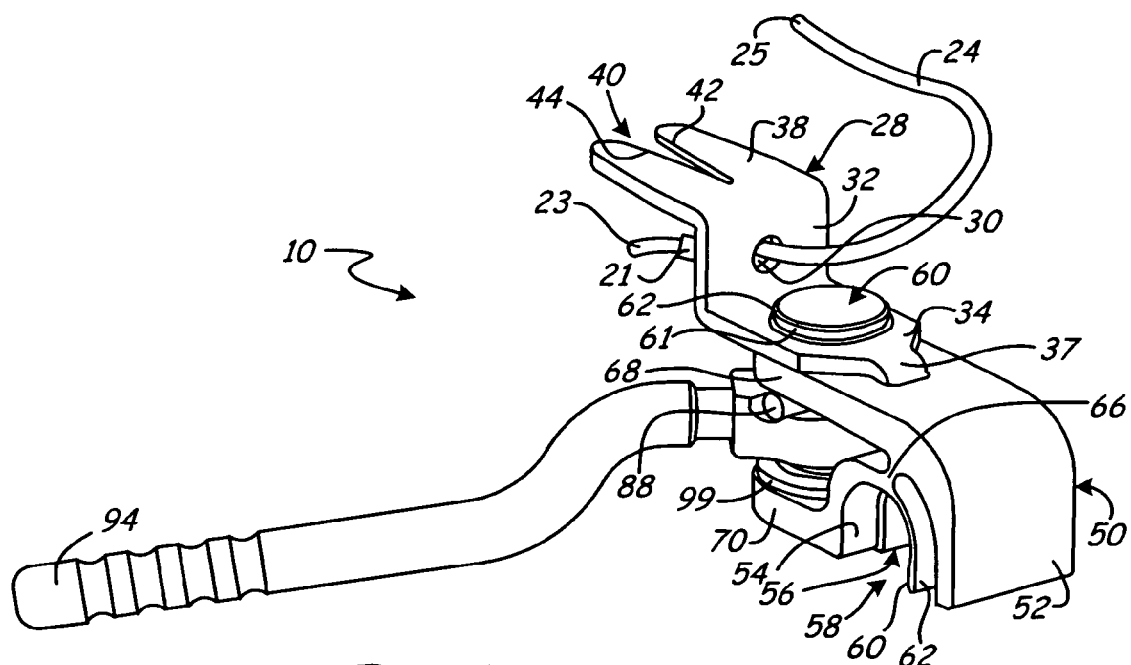
FIG. 2 is a perspective view of the retractor retaining device of the present invention.
Figure 3:
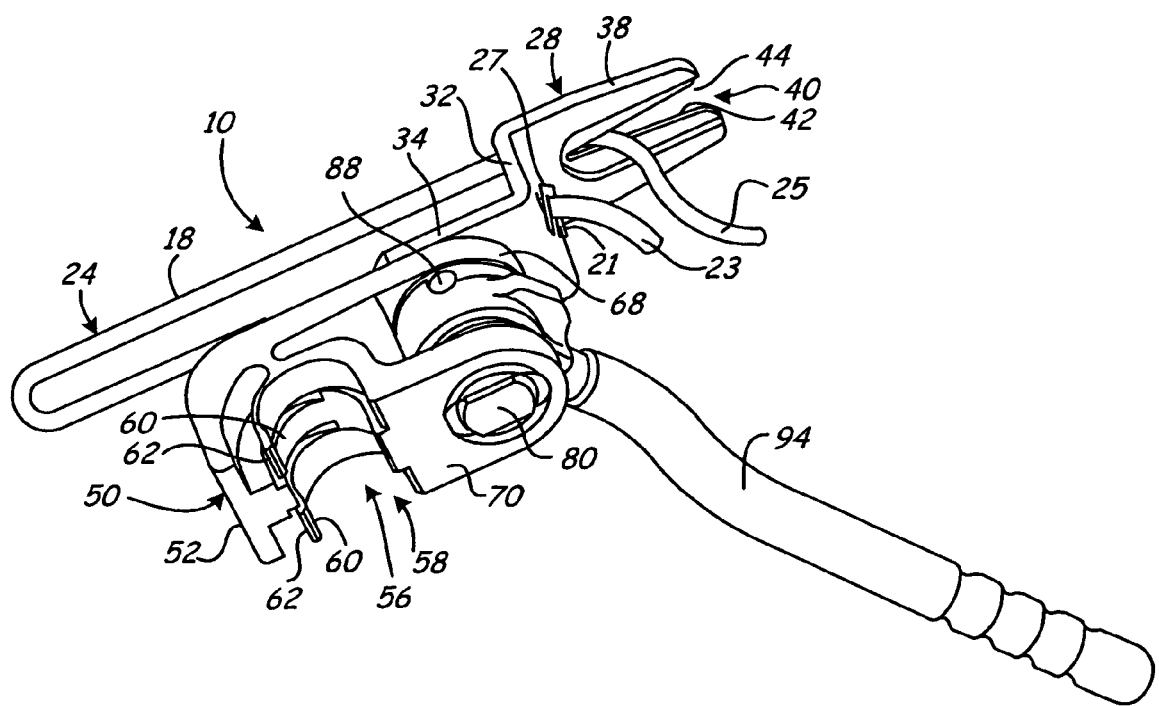
FIG. 3 is an additional perspective view of the retractor retaining device of the present invention.

Referring to FIGS. 1-3, the length or size of the loop 18 is adjustable by positioning a portion of the cord 24 into a substantially V-shaped notch 40 in an upper portion 38 of the retaining plate 28 that extends from the middle portion 32. For adjustability, the cord 24 is detachably attachable to the retaining plate 28 in a quick connect/disconnect fashion with the engagement of the cord 24 with the substantially V-shaped notch 40. The detachable attachment serves at least two purposes. The first is that the size of the loop 18 is adjustable to accommodate different diameters of retractor handles 20 and second to quickly and easily encircle the handle 20 in a plurality of selected positions with the cord 24.

The cord 24 may be constructed of any material capable of forming the loop 18 and retaining the retractor 12 in a retraction position. The cord 24 may be constructed of a polymeric material, a leather material or a cloth material on any combination thereof. The cord 24 is preferably a polymeric material having elastic qualities such as stretchability or compressability to provide additional force upon the handle 20 when secured within the V-shaped notch 40. However, an inelastic cord 24 as well as a non-stretchable and non-compressible cord 24 are also within the scope of the present invention. Further, the cord may be constructed of two or more segments of different material such as a stretchable portion and a non-stretchable portion.

A preferred method of quickly detachably attaching the cord 24 to the retaining plate 28 is to frictionally secure the cord 24 within the V-shaped notch 40 in the upper portion 38 of the retaining plate 28. The cord 24 is secured at the selected position by positioning the cord 24 into the V-shaped notch 40 with the V-shaped notch 40 engaging the cord 24 as the cord 24 is pulled into a progressively smaller area of the V-shaped notch 40.

The slight compressibility of the cord 24 also aids in engagement of the cord 24 with the V-shaped notch 40. The V-shaped notch 40 is defined by oppositely facing surfaces 42 and 44 such that when the cord 24 is pulled into engagement with the oppositely facing surfaces 42, 44, the cord 24 is retained within the V-shaped notch 40. The cord 24 is easily detachable from the V-shaped notch 40 by pulling outwardly in a direction indicated by arrow 46 as illustrated in FIG. 1. Thereby, the loop 18 is quickly formed and disposed about the handle 20 of the retractor 12, is made to fit the size of the retractor handle 20 and secures the handle 20 in one of a plurality of selected positions.

Besides a frictional engagement of the cord 24 within the V-shaped slot 40, other fastening mechanisms are also within the scope of the present invention, including a hook and loop fastener such as sold under the Velcro® trademark where one part of the fastener is secured to the clamp 50 and the other part of the fastener is secured to or is a portion of the cord 24. Other fasteners are also within the scope of the present invention including but not limited to a plurality of snaps attached to the cord 24 or the cord 24 having a plurality of apertures that engage a peg extending from the clamp 50.

Figure 6:
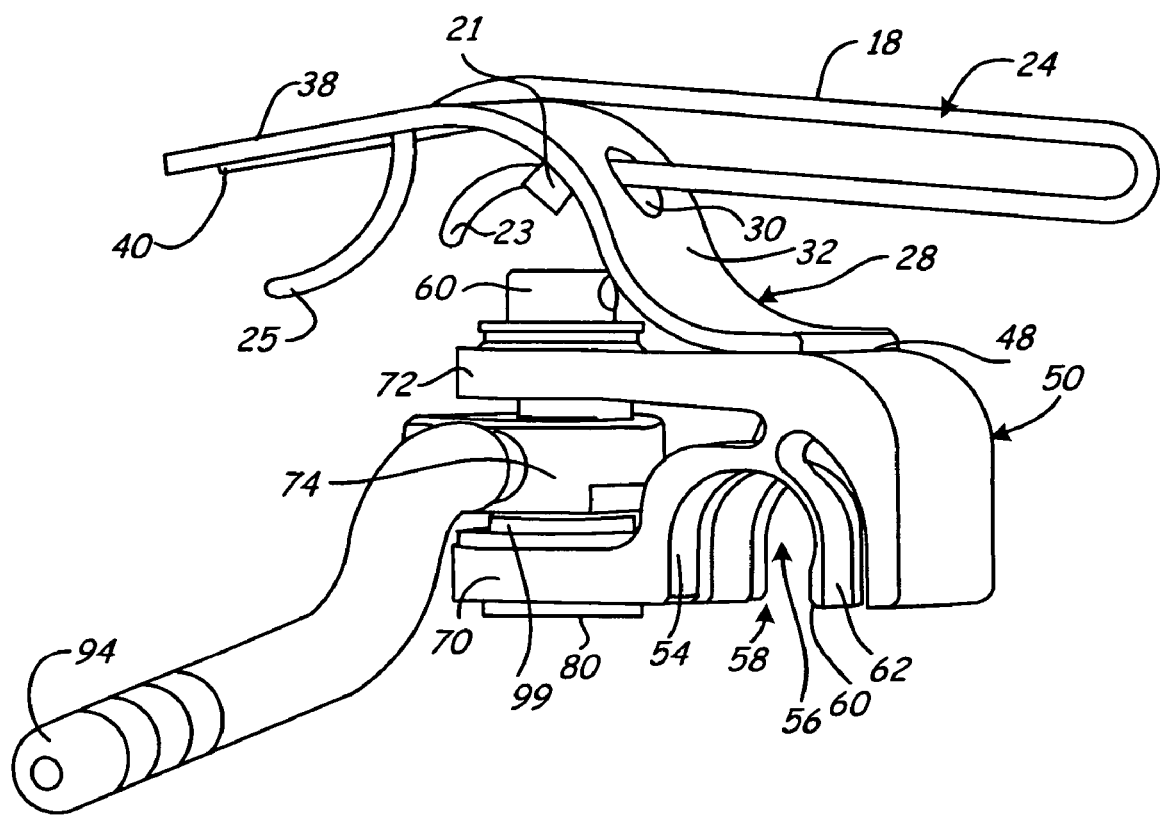
FIG. 6 is a perspective view of an alternative embodiment of the retractor retaining device of the present invention.
Figure 7:
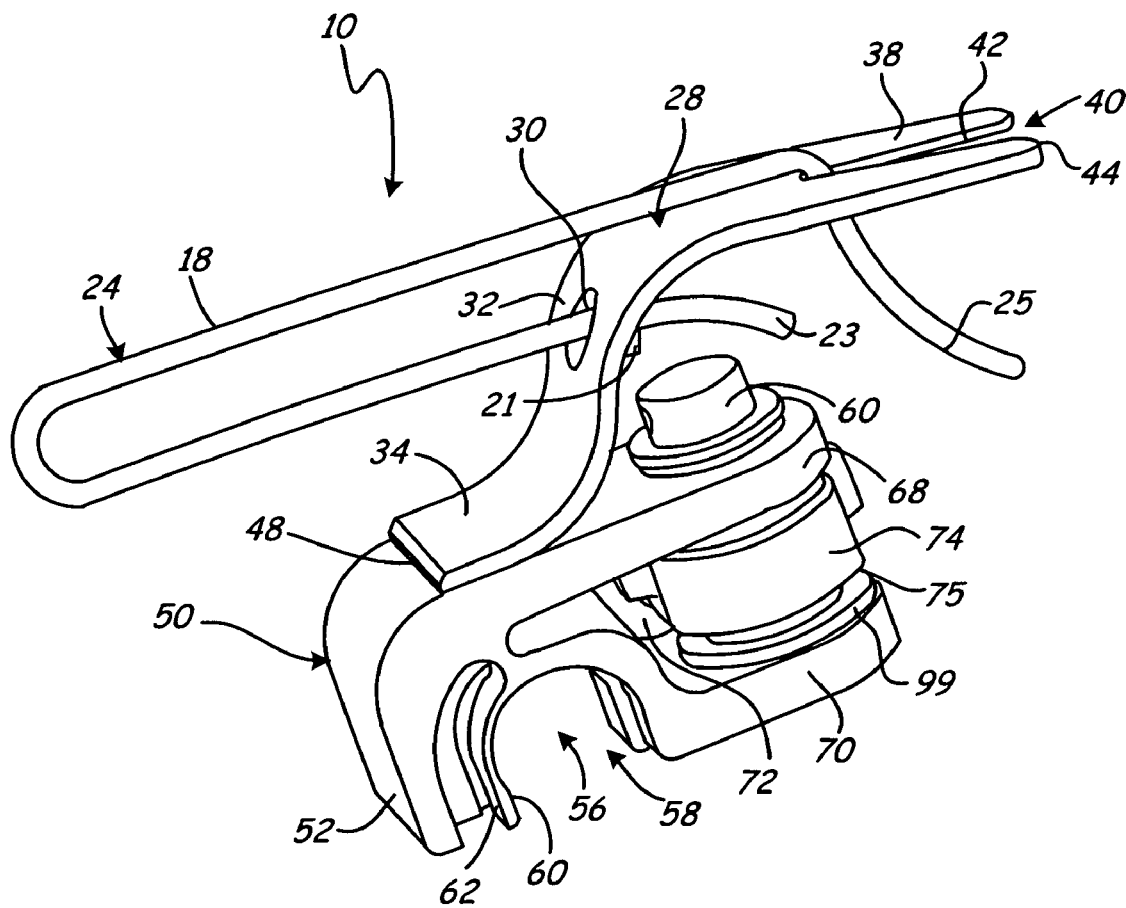
FIG. 7 is another perspective view of the alternative embodiment of the retractor retaining device of the present invention.
Figure 8:
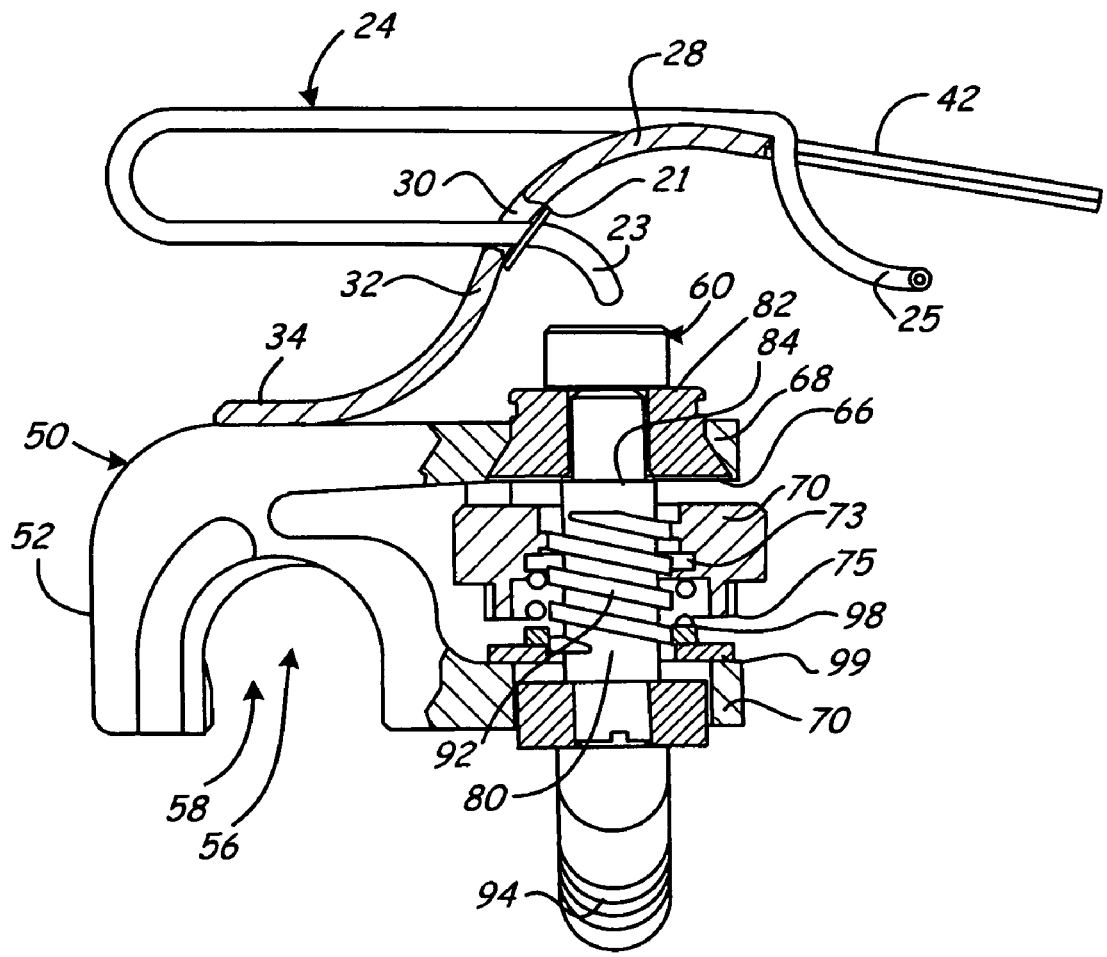
FIG. 8 is a sectional view of the alternative embodiment of the retractor retaining device of the present invention.

Referring to FIGS. 6-8, the retaining plate 28 may also be fixedly attached to the clamp 50, preferably with a weld 48. The retaining plate 28 may also be attached to the clamp 50 with a number of different securing mechanisms including but not limited to a rivet, a bolt, an adhesive and a clamping device.

Referring back to FIGS. 1-5, the clamp 50 is positioned in a selected position on the retractor support arm 15 by positioning a clamping end 52 proximate the retractor support arm 15. The clamp 50 may also be positioned on the support arm 17.

A clamping surface 54 proximate the clamping end 52 defines a clamping socket 56 that is positioned about the portion of the retractor support arm 15. By socket is meant an opening or a cavity into which an inserted part, such as a retractor support apparatus, is designed to fit and wherein the retractor support apparatus can be inserted into the socket from an infinite number of directions in a 180° range starting from a substantially parallel position to a back surface of the socket to a position substantially perpendicular to the back surface and continuing to position again substantially parallel to the back surface of the socket.

The clamping surface 54 is configured to generally conform to the cross-sectional configuration of the retractor support arm 15, but may be configured to conform to other shaped cross-sections. In the exemplary embodiment, the clamping surface 54 conforms to a substantially circular cross-section of the retractor support arm 15.

The clamping socket 56 permits the clamp 50 to be placed on the retractor support arm 15 without moving any other surgical equipment that may have been previously positioned upon the retractor support arm 15. When the clamp 50 is in a non-clamping position, the clamp 50 is retained on the retractor support arm 15 by a constricted entrance 58 to the clamping socket 56.

In an exemplary embodiment, a bead 60 is positioned upon lengths of resilient portions 62 that move as a retractor support apparatus 14 is positioned within the clamping socket 56 where the bead 60 constricts the entrance 58. However, other devices that constrict the entrance 58 to the clamping socket 56 are within the scope of the present invention including, but not limited to, a clip, a roller, a raised surface or a spring loaded device.

The constricted entrance 58 provides a preliminary clamping force around the portion of the retractor support arm 15 such that the constricted entrance 58 to the clamping socket 56 prevents the clamp 50 from slipping off the retractor support arm 15 when the clamp 50 is in a non-clamping position. The entrance 58 to the clamping socket 56 should not be so constricted to prevent use of manual force to position the clamp 50 about the portion of the retractor support arm 15. However, the entrance 58 to the clamping socket 56 should be sufficiently constricted to prevent the clamp 50 from accidentally slipping off of the retractor support arm 15. An exemplary amount of constriction of the entrance 58 to the clamping socket 56 is between about 0.010 inches and 0.020 inches and preferably about 0.015 inches.

The clamp 50 also includes an attachment end 64 and a fulcrum portion 66 between the clamping end 52 and the attachment end 64. The clamp 50 has a recess 72 defined by the upper leg 68 and a lower leg 70 proximate the attachment end 64.

The fulcrum portion 66 extends between the upper leg 68 and the lower leg 70. The fulcrum portion 66 allows the upper leg 68 to move with respect to the lower leg 70 so that the retractor support apparatus 16 is clamped within the clamping socket 56 by the clamping surface 54.

An actuating mechanism 74 is positioned within the recess 72 between the upper leg 68 and the lower leg 70 of the clamp 50. The actuating mechanism 74 is movable within the recess 72 and forces the upper and lower legs 68, 70, respectively, apart and causes the fulcrum portion 66 to flex. As the fulcrum portion 66 flexes the clamping socket 56 constricts and the clamping surface 54 frictionally engages the retractor support arm 15 in a clamped relationship.

Referring to FIGS. 3-5, the actuating mechanism 74 is positioned about a shaft 80 extending through the recess 72 and having an end 82 positioned within a cavity 65 in the peg 60. As the actuating mechanism 74 rotates about the shaft 80, the actuating mechanism 74 moves axially downward along the shaft 80 such that a bottom surface 75 of the actuating mechanism 74 engages the lower leg portion 70 and forces a shoulder 84 on the shaft 80 into a bottom surface 66 of the peg 60. With the actuating mechanism 74 rotated into the clamping position, a distance between the shoulder 84 of the shaft 80 and the bottom surface 75 of the actuating mechanism 74 is greater than a distance between the upper and lower leg portions 68, 70 and thereby causes the upper and lower leg portions 68, 70 to move in opposing directions. As the upper and lower leg portions 68, 70 are forced apart, the fulcrum portion 66 flexes and constricts the clamping socket 56 resulting in a frictional engagement of the clamping surface 54 to the retractor support 16.

The actuating mechanism 74 includes two axially symmetric ramped surfaces 76, 78 that engage a pin 88 positioned through an aperture 86 in the shaft 80. As the actuating mechanism 74 is rotated, the ramped surfaces 76, 78 engage the pin 88 such that the actuating mechanism 74 is forced down the shaft 80 until the clamp 50 is in the clamping position.

Referring to FIG. 8, the actuating mechanism 74 may alternatively include a threaded bore 73 engaging a threaded portion 92 of the shaft 80. As the actuating mechanism 74 is rotated, the threadable engagement forces the actuating mechanism 74 axially along the shaft 80 until the bottom surface 75 of the actuating mechanism 74 engages the lower leg portion 70. As the bottom surface 75 engages the lower leg portion 70, the shoulder 84 of the shaft 80 engages the bottom surface 66 of the peg 60 which forces the upper leg portion 68 and the lower leg portions 70 to move in opposing directions which causes the fulcrum portion 66 to flex and the clamping socket 58 to constrict.

Other types of clamps and actuating mechanisms may be used to practice the present invention. For example, a clamp having a clamping bore may be used to practice the present invention.

In operation, the actuating mechanism 74 is positioned in a non-clamping position. With the actuating mechanism 74 in the non-clamping position, the clamp 50 can accept the retractor support arm 15.

The clamp 50 is disposed in a selected position on the retractor support arm 15 by positioning the constricted entrance 58 of the clamping socket 56 proximate the retractor support arm 15. Manual force is applied to the clamp 50 substantially perpendicular to an axis 17 of the retractor support arm 15 to overcome the constricted entrance 58 of the clamping socket 56, thereby disposing the clamp 50 about the retractor support arm 74. With the actuating mechanism 74 in the non-clamping position, the clamp 50 is slidably positionable on the retractor support arm 15.

To position the actuating mechanism 74 into the clamping position, a handle 94 fixedly attached to the actuating mechanism 74 is moved in a direction of arrows 96 as illustrated in FIG. 1, which rotates the actuating mechanism 74 about the shaft 80. As the actuating mechanism 74 rotates about the shaft 80, the actuating mechanism 74, depending upon the design, engages either the pin 88 or the threaded region 92 on the shaft 80 and forces the actuating mechanism 74 towards the lower leg 70. As the actuating mechanism 74 engages the lower leg 70, a force is placed upon the lower leg 70, the actuating mechanism 74 and the shaft 80. A maximum force is placed upon the lower leg 70, the actuating mechanism 74 and the shaft 78 when the actuating mechanism 74 is rotated approximately 180 degrees opposite the non-clamping position wherein the lower surface 75 of the actuating mechanism 74 contacts an inner surface 71 of the lower leg 70.

With the actuating mechanism 74 in the clamping position, the distance between the shoulder 84 and the bottom surface 75 of the actuating mechanism 74 is greater than the distance between the upper and lower legs 68, 70 such that the upper and lower legs 68, 70, are forced apart transferring the force from the shaft 78 to the upper leg 68. With the upper and lower legs 68, 70 forced apart, the fulcrum portion 66 flexes which causes the clamping socket 56 to constrict such that the clamp 50 frictionally engages the retractor support arm 50.

With the clamp 50 secured to the support arm 15, the retractor 12 is manually positioned within the surgical wound 16 and manual force is applied to the retractor 12 to retract flesh. With the retractor 12 in the selected position, the loop 18 is formed about the handle 20 by securing the cord 24 within the V-shaped slot 40. To remove the retractor 12 from the surgical wound 16, the cord 24 is disengaged from the V-shaped slot 40 such that the retractor handle 20 is disengaged from the cord 24.

The clamp 50 may also have a compression spring 98 positioned about the shaft 80 and between the lower leg 70 and the actuating mechanism 74 to bias the actuating mechanism 74 toward the clamping position. A washer 99 may also optionally be positioned about the shaft 80 and between the lower leg portion 70 and the actuating mechanism 74 to prevent the actuating mechanism 74 and the lower leg portion 70 from galling over time with use.

Although the present invention has been described with reference to preferred embodiments, workers skilled in the art will recognize that changes may be made in form and detail without departing from the spirit and scope of the invention.

What is claimed is:

1. A retractor retaining device for retaining a retractor from a table mounted retractor support in a retraction position within a surgical wound, the device comprising:

a clamp attachable to the retractor support;

a retaining plate attached to the clamp; and a flexible loop detachably attached at one end to the retaining plate for engaging a proximal end of the retractor such that the retractor is retained in the retraction position.

2. The device of claim 1 wherein the flexible loop is attached to the retaining plate such that the loop may be adjusted in size for engaging the proximal end of the retractor.

3. The device of claim 1 and wherein the clamp comprises a clamping socket that engages and attaches the clamp to the retractor support.

4. The device of claim 3 wherein the clamp comprises a fulcrum portion that flexes and constricts the clamping socket when the clamp is positioned into the clamping position.

5. The device of claim 1 and wherein the retaining plate removably attaches to the clamp.

6. The device of claim 1 wherein the retaining plate fixedly attaches to the clamp.

7. The device of claim 1 wherein the loop includes a flexible cord attached to the retaining plate at a first end and detachably attached to the retaining plate at a second end such that the length of the loop is adjustable.

8. The device of claim 7 wherein the retaining plate includes a substantially V-shaped slot and wherein the second end of the loop is engageable within the V-type slot such that the second end of the cord is detachably attached to the main body.

9. A retraction device comprising:

a retractor support member for positioning near a surgical wound;

a clamp secured to the retractor support member and having a retaining plate attached thereto;

a retractor having a proximal end and a distal end, the distal end for insertion into the surgical wound; and a flexible loop secured to the retaining plate for engaging the proximal end of the retractor in a manner that retains the retractor in a retraction position within a surgical wound.

10. The device of claim 9 wherein the flexible loop is attached to the retaining plate such that the loop may be adjusted in size for engaging the proximal end of the retractor.

11. The device of claim 10 and wherein the retaining plate further comprises an attaching mechanism that engages and retains the flexible loop to the retaining plate.

12. The device of claim 9 and wherein the retaining plate removably attaches to the clamp.

13. The device of claim 9 and wherein the retaining plate fixedly attaches to the clamp.

14. The device of claim 9 wherein the loop includes a flexible cord having a band attached proximate an end thereof and wherein the cord positions through an aperture in the retaining plate and wherein the band has length that prevents the end from passing through the aperture and thereby retains the flexible cord to the retaining plate and wherein another end is detachably attached to the attaching mechanism at a second end such that the length of the loop is adjustable.

15. The device of claim 14 wherein the retaining plate includes a substantially V-type slot and wherein the second end of the loop is engageable within the V-type slot such that the second end of the cord is detachably attached to the attaching mechanism.

16. A method of holding a surgical retractor in a refraction position within a surgical wound, the method comprising:

providing a support member near the surgical wound;

positioning a clamp on the support member and wherein the clamp includes a retaining plate attached to the clamp;

inserting a distal end of a retractor within the surgical wound and manually positioning the retractor in the retraction position; and securing the retractor in the retraction position by engaging a proximal end of the retractor with a flexible loop that is attached to the retaining plate.

17. The method of claim 16 and further comprising:

adjusting the size of the loop by disengaging one end of the loop from the retaining plate and re-engaging the loop to the retaining plate with a different loop length.

18. The device of claim 17 wherein the clamp comprises a clamping socket for engaging the retractor support member.

19. The device of claim 18 wherein the clamp further comprises a fulcrum portion and wherein the fulcrum portion flexes and constricts the clamping socket when the clamp is positioned into a clamping position.

20. The method of claim 16 wherein the loop is engaged or disengaged from the retaining plate by engaging or disengaging a V-shaped slot within the retaining plate.

* * * * *

UNITED STATES PATENT AND TRADEMARK OFFICE
CERTIFICATE OF CORRECTION

| | | |
|---|---|---|
| PATENT NO. | : 7,309,312 B2 | Page 1 of 1 |
| APPLICATION NO. | : 11/034234 | |
| DATED | : December 18, 2007 | |
| INVENTOR(S) | : Todd M. Bjork et al. | |

It is certified that error appears in the above-identified patent and that said Letters Patent is hereby corrected as shown below:

Claim 16, column 8, line 19, change "A method of holding a surgical retractor in refraction" to --A method of holding a surgical retractor in retraction--.

Signed and Sealed this

Sixteenth Day of June, 2009

JOHN DOLL
*Acting Director of the United States Patent and Trademark Office*